United States Patent [19]
Mayer et al.

[11] Patent Number: 5,922,546
[45] Date of Patent: Jul. 13, 1999

[54] HUMAN DISINTEGRIN METALLOPROTEASE KUZ GENE

[75] Inventors: Ruth Judik Mayer, Wayne; Jeffrey Richard Jackson, Collegeville, both of Pa.; Catherine Elizabeth Ellis, Glassboro, N.J.

[73] Assignee: Smithkline Beecham Corporation, Philadelphia, Pa.

[21] Appl. No.: 08/920,234

[22] Filed: Aug. 25, 1997

[51] Int. Cl.[6] ............ C12N 15/00; C12N 15/85; C12Q 1/68; C07K 16/00
[52] U.S. Cl. ............ 435/6; 435/219; 435/320.1; 435/325; 435/455; 530/387.1; 530/388.15; 536/23.1; 536/23.2; 536/23.5
[58] Field of Search ............... 435/6, 69.1, 219, 435/226, 172.1, 172.3, 325, 320.1, 455, 366, 368; 536/23.2, 23.1, 23.5, 24.31; 530/387.1, 387.9, 388.15, 388.2, 388.26

[56] References Cited

PUBLICATIONS

GenBank Accession No. Z48579.
GenBank Accession No. Z21961.
Howard, L. et al. "Molecular cloning of MADM: a catalytically active mammalian disintegrin etalloprotase expressed in various cell types", Biochem, J. 317,45–50, 1996.
Lunn, C.A., et al., "Purification of ADAM 10 from bovine spleen as a TNFα convertase", FEBS Letters, 400:333–335, 1997.
Fambrough et al., The Cell Surface Metalloprotease/Disintegrin Kuzbanian is Required for Axonal Extension in Drosophila, PNAS 91, 13233–38 (Nov. 1996).
R.F. Doolittle, Of URFS and ORFS, A Primer on How to Analyze Derived Amino Acid Sequences, University Science Books (1986), at p. 7.
Robbins and Cotran, Pathological Basis of Disease, W.B. Saunders Co., Phila (1976), pp. 55, 279, 1530.
Glynn et al., PIR, Accession Nos. S66129, S32205, Jul. 19, 1996.

*Primary Examiner*—John L. LeGuyader
*Assistant Examiner*—Mark G. Shibuya
*Attorney, Agent, or Firm*—Elizabeth J. Hecht; Ratner & Prestia; William T. King

[57] ABSTRACT

Human KUZ polypeptides and polynucleotides and methods for producing such polypeptides by recombinant techniques are disclosed. Also disclosed are methods for utilizing Human KUZ polypeptides and polynucleotides in the design of protocols for the treatment of inflammation, neural degeneration, allergic disorders, or other disorders involving a dis-regulation of the substrate cytokines or receptors, among others, and diagnostic assays for such conditions.

20 Claims, No Drawings

HUMAN DISINTEGRIN METALLOPROTEASE KUZ GENE

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the ADAM family of metalloproteases, hereinafter referred to as Human KUZ. The invention also relates to inhibiting or activating the action of such polynucleotides and polypeptides.

BACKGROUND OF THE INVENTION

The protein known as the human homolog of the Drosophila KUZ gene is a member of the ADAM family of metalloproteases. This protease and another family member, TNF converting enzyme, have been shown to be capable of processing pro-TNF to the mature form of TNF (Black et al. Nature 385:729, 1997; Lunn et al., FEBS Lett. 400: 333–335, 1997). Therefore, this and additional family members would be expected to have a role in the processing of other cytokines, growth factors, or receptors. Other cytokines or receptors in which processing occurs and in which the biochemistry is consistent with a mechanism involving ADAM family members include CD23, L-selectin, FAS ligand, CD16 and others (reviewed in Hooper et al., Biochem J. 321, 265–279, 1997). The relationship between the possible substrates and ADAM family members is unknown, so that human KUZ protein may participate in the processing of any combination of these cytokines and growth factors in one or more cell types. Other family members, meltrin and fertilin, are involved in cell-cell fusion (Yagami-Hiromasa et al. Nature 377: 652–656 (1995). The bovine homolog of the human KUZ protein has been shown to use myelin as a substrate (Howard et al., Biochem J. 317: 45–50, 1996) and the Drosophila KUZ gene product is involved in neural differentiation (Rooke et al. Science 273: 1227–1231, 1996). Inhibition of one or more of these processing enzymes could have therapeutic utility in inflammation, neural degeneration, allergic disorders, or other disorders involving a dis-regulation of the substrate cytokines or receptors.

This indicates that the ADAM family has an established, proven history as therapeutic targets. Clearly there is a need for identification and characterization of further members of the ADAM family which can play a role in preventing, ameliorating or correcting dysfunctions or diseases, including, but not limited to, inflammation, neural degeneration, allergic disorders, or other disorders involving a dis-regulation of the substrate cytokines or receptors.

SUMMARY OF THE INVENTION

In one aspect, the invention relates to Human KUZ polypeptides and recombinant materials and methods for their production. Another aspect of the invention relates to methods for using such Human KUZ polypeptides and polynucleotides. Such uses include the treatment inflammation, neural degeneration, allergic disorders, or other disorders involving a dis-regulation of the substrate cytokines or receptors, among others. In still another aspect, the invention relates to methods to identify agonists and antagonists using the materials provided by the invention, and treating conditions associated with Human KUZ imbalance with the identified compounds. Yet another aspect of the invention relates to diagnostic assays for detecting diseases associated with inappropriate Human KUZ activity or levels.

DESCRIPTION OF THE INVENTION

Definitions

The following definitions are provided to facilitate understanding of certain terms used frequently herein.

"Human KUZ" refers, among others, generally to a polypeptide having the amino acid sequence set forth in SEQ ID NO: 2 or an allelic variant thereof.

"Human KUZ activity or Human KUZ polypeptide activity" or "biological activity of the Human KUZ or Human KUZ polypeptide" refers to the metabolic or physiologic function of said Human KUZ including similar activities or improved activities or these activities with decreased undesirable side-effects. Also included are antigenic and immunogenic activities of said Human KUZ.

"Human KUZ gene" refers to a polynucleotide having the nucleotide sequence set forth in SEQ ID NO: 1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to Human KUZ polypeptides (or Human KUZ proteins). The Human KUZ polypeptides include the polypeptide of SEQ ID NO: 2; as well as polypeptides comprising the amino acid sequence of SEQ ID NO: 2; and polypeptides comprising the amino acid sequence which have at least 80% identity to that of SEQ ID NO: 2 over its entire length, and still more preferably at least 90% identity, and even still more preferably at least 95% identity to SEQ ID NO: 2. Furthermore, those with at least 97–99% are highly preferred. Also included within Human KUZ polypeptides are polypeptides having the amino acid sequence which have at least 80% identity to the polypeptide having the amino acid sequence of SEQ ID NO: 2 over its entire length, and still more preferably at least 90% identity, and still more preferably at least 95% identity to SEQ ID NO: 2. Furthermore, those with at least 97–99% are highly preferred. Preferably Human KUZ polypeptide exhibit at least one biological activity of Human KUZ.

The Human KUZ polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the Human KUZ polypeptides are also included in the invention. A fragment is a polypeptide having an amino acid sequence that entirely is the same as part, but not all, of the amino acid sequence of the aforementioned Human KUZ polypeptides. As with Human KUZ polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of Human KUZ polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of Human KUZ polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate Human KUZ activity, including those with a similar activity or an improved activity, or with a decreased undesirable activity. Also included are those that are antigenic or immunogenic in an animal, especially in a human.

Preferably, all of these polypeptide fragments retain the biological activity of the Human KUZ, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The Human KUZ polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to Human KUZ polynucleotides. Human KUZ polynucleotides include isolated polynucleotides which encode the Human KUZ polypeptides and fragments, and polynucleotides closely related thereto. More specifically, Human KUZ polynucleotide of the invention include a polynucleotide comprising the nucleotide sequence contained in SEQ ID NO: 1 encoding a Human KUZ polypeptide of SEQ ID NO: 2, and polynucleotide having the particular sequence of SEQ ID NO: 1. Human KUZ polynucleotides further include a polynucleotide comprising a nucleotide sequence that has at least 80% identity over its entire length to a nucleotide sequence encoding the Human KUZ polypeptide of SEQ ID NO: 2, and a polynucleotide comprising a nucleotide sequence that is at least 80% identical to of SEQ ID NO: 1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under Human KUZ polynucleotides are a nucleotide sequence which has sufficient identity to a nucleotide sequence contained in SEQ ID NO: 1 to hybridize under conditions useable for amplification or for use as a probe or marker. The invention also provides polynucleotides which are complementary to such Human KUZ polynucleotides.

Human KUZ of the invention is structurally related to other proteins of the ADAM family, as shown by the results of sequencing the cDNA of Table 1 (SEQ ID NO: 1) encoding human KUZ. The cDNA sequence of SEQ ID NO: 1 contains an open reading frame (nucleotide number 113 to 2356) encoding a polypeptide of 748 amino acids of SEQ ID NO: 2. The amino acid sequence of Table 2 (SEQ ID NO: 2) has about 97% identity (using BLAST) in 748 amino acid residues with B. taurus metalloprotease (Howard, L. et al., Biochem J. 317, 45–50, (1996)) and 99% identity over 589 amino acid residues to the partial human clone for disintegrin metalloprotease (GenBank Z48579). Furthermore, Human KUZ (SEQ ID NO: 2) is 49% identical to the Drosophila KUZ gene over 589 amino acid residues (Rooke, J. et al, Science 273, 1227–1231, 1996). In addition, Human KUZ (SEQ ID NO: 2) is 25% identical to TNF-alpha converting enzyme over 805 amino acids residues (Black, R. et al. Nature, 385: 729–733, 1997; Moss, M. L. et al., Nature 385: 733–736, 1997). The nucleotide sequence of Table 1 (SEQ ID NO: 1) has about 94% identity (using BLAST) in 2255 nucleotide residues with B. taurus metalloprotease (Howard, L. et al., Biochem J. 317, 45–50, (1996)); 100% identity in 2116 nucleotide residues to the partial human clone for disintegrin metalloprotease (GenBank Z48579). Thus Human KUZ polypeptides and polynucleotides of the present invention are expected to have, inter alia, similar biological functions/properties to their homologous polypeptides and polynucleotides, and their utility is obvious to anyone skilled in the art.

TABLE 1[a]

GTCCCGGCTTCCCGTGGAGGCTCCGGACCAAGCCCCTTCAGCTTCTCCCTCCGGATCGAT
GTGCTGCTGTTAACCCGTGAGGAGGCGGCGGCGGCGGCAGCGGCAGCGGAAGATGGTGTT
GCTGAGAGTGTTAATTCTGCTCCTCTCCTGGGCGGCGGGGATGGGAGGTCAGTATGGGAA
TCCTTTAAATAAATATATCAGACATTATGAAGGATTATCTTACAATGTGGATTCATTACA
CCAAAAACACCAGCGTGCCAAAAGAGCAGTCTCACATGAAGACCAATTTTTACGTCTAGA
TTTCCATGCCCATGGAAGACATTTCAACCTACGAATGAAGAGGGACACTTCCCTTTTCAG
TGATGAATTTAAAGTAGAAACATCAAATAAAGTACTTGATTATGATACCTCTCATATTTA
CACTGGACATATTTATGGTGAAGAAGGAAGTTTTAGCCATGGGTCTGTTATTGATGGAAG
ATTTGAAGGATTCATCCAGACTCGTGGTGGCACATTTTATGTTGAGCCAGCAGAGAGATA
TATTAAAGACCGAACTCTGCCATTTCACTCTGTCATTTATCATGAAGATGATATTAACTA
TCCCCATAAATACGGTCCTCAGGGGGGCTGTGCAGATCATTCAGTATTTGAAAGAATGAG
GAAATACCAGATGACTGGTGTAGAGGAAGTAACACAGATACCTCAAGAAGAACATGCTGC
TAATGGTCCAGAACTTCTGAGGAAAAAACGTACAACTTCAGCTGAAAAAAATACTTGTCA
GCTTTATATTCAGACTGATCATTTGTTCTTTAAATATTACGGAACACGAGAAGCTGTGAT
TGCCCAGATATCCAGTCATGTTAAAGCGATTGATACAATTTACCAGACCACAGACTTCTC
CGGAATCCGTAACATCAGTTTCATGGTGAAACGCATAAGAATCAATACAACTGCTGATGA
GAAGGACCCTACAAATCCTTTCCGTTTCCCAAATATTGGTGTGGAGAAGTTTCTGGAATT
GAATTCTGAGCAGAATCATGATGACTACTGTTTGGCCTATGTCTTCACAGACCGAGATTT
TGATGATGGCGTACTTGGTCTGGCTTGGGTTGGAGCACCTTCAGGAAGCTCTGGAGGAAT
ATGTGAAAAAAGTAAACTCTATTCAGATGGTAAGAAGAAGTCCTTAAACACTGGAATTAT
TACTGTTCAGAACTATGGGTCTCATGTACCTCCCAAAGTCTCTCACATTACTTTTGCTCA
CGAAGTTGGACATAACTTTGGATCCCCACATGATTCTGGAACAGAGTGCACACCAGGAGA
ATCTAAGAATTTGGGTCAAAAAGAAAATGGCAATTACATCATGTATGCAAGAGCAACATC
TGGGGACAAACTTAACAACAATAAATTCTCACTCTGTAGTATTAGAAATATAAGCCAAGT
TCTTGAGAAGAAGAGAAACAACTGTTTTGTTGAATCTGGCCAACCTATTTGTGGAAATGG
AATGGTAGAACAAGGTGAAGAATGTGATTGTGGCTATAGTGACCAGTGTAAAGATGAATG
CTGCTTCGATGCAAATCAACCAGAGGGAAGAAAAATGCAAACTGAAACCTGGGAAACAGTG
CAGTCCAAGTCAAGGTCCTTGTTGTACAGCACAGTGTGCATTCAAGTCAAAGTCTGAGAA
GTGTCGGGATGATTCAGACTGTGCAAGGGAAGGAATATGTAATGGCTTCACAGCTCTCTG
CCCAGCATCTGACCCTAAACCAAACTTCACAGACTGTAATAGGCATACACAAGTGTGCAT
TAATGGGCAATGTGCAGGTTCTATCTGTGAGAAATATGGCTTAGAGgAGTGTACGTGTGC
CAGTTCTGATGGCAAAGATGATAAAGAATTATGCCATGTATGCTGTATGAAGAAAATGGA
CCCATCAACTTGTGCCAGTACAGGGTCTGTGCAGTGGAGTAGGCACTTCAGTGGTCGAAC
CATCACCCTGCAACCTGGATCCCCTTGCAACGATTTTAGAGGTTACTGTGATGTTTTCAT
GCGGTGCAGATTAGTAGATGCTGATGGTCCTCTAGCTAGGCTTAAAAAaGCAATTTTTAG
TCCAGAGCTCTATGAAAACATTGCTGAATGGATTGTGGCTCATTGGTGGGCAGTATTACT
TATGGGAATTGCTCTGATCATGCTAATGGCTGGATTTATTAAGATATGCAGTGTTCATAC
TCCAAGTAGTAATCCAAAGTTGCCTCCTCCTAAACCACTTCCAGGCACTTTAAAGAGGAG
GAGACCTCCACAGCCCATTCAGCAACCCCAGCGTCAGCGGCCCCGAGAGAGTTATCAAAT
GGGACACATGAGACGCTAACTGCAGCTTTTGCCTTGGTTCTTCCTAGTGCCTACAATGGG
AAAACTTCACTCCAAAGAGAAACCTATTAAGTCATCATCTCCAAACTAAACCCTCACAAG
TAACAGTTGAAGAAAAAATGGCAAGAGATCATATCCTCAGACCAGGTGGAATTACTTAAA
TTTTAAAGCCTGAAAATTCCAATTTGGGGGTGGGAGGTGGAAAAGGAACCCAATTTTCTT
ATGAACAGATATTTTTAACTTAATGGCACAAAGTCTTAGAATATTATTATGTGCCCCGTG
TTCCCTGTTCTTCGTTGCTGCATTTTCTTCACTTGCAGGCAAACTTGGCTCTCAATAAAC
TTTTACCACAAATTGAAATAAATATATTTTTTTCAACTGCCAATCAAGGGTAGGAGGCTC
GACCACCTCAACATTGGAGACATCACTTGCCAATGTACATACCTTGTTATATGCAGACAT
GTATTTCTTACGTACACTGTACTTCTGTGTGCAATTGTAAACAGAAATTGCAATATGGAT
GTTTCTTTGTATTATAAAATTTTTCCGCTCTTAATTAAAAATTACTGTTTAATTGACATA
CTCAGGATAACAGAGAATGGTGGTATTCAGTGGTCCAGGATTCTGTAATGCTTTACACAG
GCAGTTTTGAAATGAAAATCAATTTACCTTTCTGTTACGATGGAGTTGGTTTTGATACTC
ATTTTTTCTTTATCACATGGCTGCTACGGGCACAAGTGACTATACTGAAGAACACAGTTA
AGTGTTGTGCAAACTGGACATAGCAGCACATACTACTTCAGAGTTCATGATGTAGATGTC
TGGTTTCTGCTTACGTCTTTTAAACTTTCTAATTCAATTCCATTTTTCAATTAATAGGTG
AAATTTATTCATGCTTTGATAGAAATTATGTCAATGAAATGAAAAAAAAAAAAAAAAAGG
GCGGCCGCTCTAGAGGATCCCTCGAGGGGCCCAAGCTTACGCGTGCATG

[a] A nucleotide of a Human KUZ (SEQ ID NO: 1).

TABLE 2[b]

MVLLRVLILLLSWAAGMGGQYGNPLNKYIRHYEGLSYNDSLHQKHQRAKRAVSHEDQFL
RLDFHAHGRHFNLRMKRDTSLFSDEFKVETSNKVLDYDTSHIYTGHIYGEEGSFSHGSVI
DGRFEGFIQTRGGTFYVEPAERYIKDRTLPFHSVIYHEDDINYPHKYGRQGGCADHSVFE
RMRKYQMTGVEETQIPQEEHAANGPELLRKKRTTSAEKNTCQLQTDHLFFYYGTRE
AVIAQISSHVKAIDTTYQTTDFSGIRNISFMVKRIRINTTADEKDPTNPFRFPNIGVEKF
LELNSEQHNHDDYCLAYVFTDRDDGVGLAWVGAPSGSSGGICEKSKLYSDGKKKSLNT
GIITVQNYGSHVPPKVSHITFAHEVGHNFGSPHDSGTECTPGESKNLGQKENGNYIMYAR
ATSGDKLNNNKFSLCSIRNISQVLEKKRNNCFVESGQPICGNGMVEQGEECDCGYSDQCK
DECCFDANQPEGRKCKLKPGKQCSPSQGPCCTAQCAFKSKSEKCRDDSDCAREGICNGFT
ALCPASDPKPNFTDCNRHTQVCINGQCAGSICEKYGLEECTCASSDGKDDKELCHVCMK
KMDPSTCASTGSVQWSRHFSGRTITLQPGSPCNDFRGYCDVFMRCRLVDADGPLARLKKA
IFSPELYENIAEWIVAHWWAVLLMGIALIMLMAGFIKICSVHTPSSNPKLPPPKPLPGTL
KRRRPPQPIQQPQRQRPRESYQMGHMRR

[b] An amino acid sequence of a Human KUZ (SEQ ID NO: 2).

One polynucleotide of the present invention encoding Human KUZ may be obtained using standard cloning and screening, from a cDNA library derived from mRNA in cells of human synovial fibroblast; human osteoclastoma; human activated monocytes; human T cells; human colon carcinoma using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding Human KUZ polypeptide of SEQ ID NO: 2 may be identical to the polypeptide encoding sequence contained in Table 1 (nucleotide number 113 to 2356 of SEQ ID NO: 1), or it may be a sequence, which as a result of the redundancy (degeneracy) of the genetic code, also encodes the polypeptide of SEQ ID NO: 2.

When the polynucleotides of the invention are used for the recombinant production of Human KUZ polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding Human KUZ variants comprise the amino acid sequence Human KUZ polypeptide of Table 2 (SEQ ID NO: 2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO: 1 or a fragment thereof, may be used as hybridization probes for cDNA and genomic DNA, to isolate full length cDNAs and genomic clones encoding Human KUZ polypeptide and to isolate cDNA and genomic clones of other genes (including genes encoding homologs and orthologs from species other than human) that have a high sequence similarity to the Human KUZ gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding Human KUZ polypeptide, including homologs and orthologs from species other than human, comprises the steps of screening an appropriate library under stingent hybridization conditions with a labeled probe having the SEQ ID NO: 1 or a fragment thereof; and isolating full-length cDNA and genomic clones containing said polynucleotide sequence. Thus in another aspect, Human KUZ polynucleotides of the present invention further include a nucleotide sequence comprising a nucleotide sequence that hybridize under stringent condition to a nucleotide sequence having SEQ ID NO: 1 or a fragment thereof. Also included with Human KUZ polypeptides are polypeptide comprising amino acid sequence encoded by nucleotide sequence obtained by the above hybridization condition. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtlilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (*supra*).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the Human KUZ polypeptide is to be expressed for use in screening assays, generally, it is preferred that the polypeptide be produced at the surface of the cell. In this event, the cells may be harvested prior to use in the screening assay. If Human KUZ polypeptide is secreted into the medium, the medium can be recovered in order to recover and purify the polypeptide; if produced intracellularly, the cells must first be lysed before the polypeptide is recovered. Human KUZ polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of Human KUZ polynucleotides for use as diagnostic reagents. Detection of a mutated form of Human KUZ gene associated with a dysfunction will provide a diagnostic tool that can add to or define a diagnosis of a disease or susceptibility to a disease which results from under-expression, over-expression or altered expression of Human KUZ. Individuals carrying mutations in the Human KUZ gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Human KUZ nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising Human KUZ nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility inflammation, neural degeneration, allergic disorders, or other disorders involving a dis-regulation of the substrate cytokines or receptors through detection of mutation in the Human KUZ gene by the methods described.

In addition, inflammation, neural degeneration, allergic disorders, or other disorders involving a dis-regulation of the substrate cytokines or receptors, can be diagnosed by methods comprising determining from a sample derived from a subject an abnormally decreased or increased level of Human KUZ polypeptide or Human KUZ mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an Human KUZ polypeptide, in a sample derived from a host are well-known to those of skill in the art. Such assay methods include radioimmunoassays, competitive-binding assays, Western Blot analysis and ELISA assays.

Thus in another aspect, the present invention relates to a diagonostic kit for a disease or suspectability to a disease, particularly inflammation, neural degeneration, allergic disorders, or other disorders involving a dis-regulation of the substrate cytokines or receptors, which comprises:

(a) a Human KUZ polynucleotide, preferably the nucleotide sequence of SEQ ID NO: 1, or a fragment thereof;

(b) a nucleotide sequence complementary to that of (a);

(c) a Human KUZ polypeptide, preferably the polypeptide of SEQ ID NO: 2, or a fragment thereof; or (d) an antibody to a Human KUZ polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the Human KUZ polypeptides. The term "immunospecific" means that the antibodies have substantial greater affinity for the polypeptides of the invention than their affinity for other related polypeptides in the prior art.

Antibodies generated against the Human KUZ polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against Human KUZ polypeptides may also be employed to treat inflammation, neural degeneration, allergic disorders, or other disorders involving a dis-regulation of the substrate cytokines or receptors, among others.

Vaccines

Another aspect of the invention relates to a method for inducing an immunological response in a mammal which comprises inoculating the mammal with Human KUZ polypeptide, or a fragment thereof, adequate to produce antibody and/or T cell immune response to protect said animal inflammation, neural degeneration, allergic disorders, or other disorders involving a dis-regulation of the substrate cytokines or receptors, among others. Yet another aspect of the invention relates to a method of inducing immunological response in a mammal which comprises, delivering Human KUZ polypeptide via a vector directing expression of Human KUZ polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a Human KUZ polypeptide wherein the composition comprises a Human KUZ polypeptide or Human KUZ gene. The vaccine formulation may further comprise a suitable carrier. Since Human KUZ polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The Human KUZ polypeptide of the present invention may be employed in a screening process for compounds which activate (agonists) or inhibit activation of (antagonists, or otherwise called inhibitors) the Human KUZ polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, receptors, enzymes, etc., as the case may be, of the polypeptide of the present invention; or may be structural or functional mimetics of the polypeptide of the present invention. See Coligan et al., Current Protocols in Immunology 1(2):Chapter 5 (1991). Human KUZ polypeptides are responsible for many biological functions, including many pathologies. Accordingly, it is desirous to find compounds and drugs which stimulate Human KUZ polypeptide on the one hand and which can inhibit the function of Human KUZ polypeptide on the other hand. In general, agonists are employed for therapeutic and prophylactic purposes for such conditions as inflammation, neural degeneration, allergic disorders, or other disorders involving a dis-regulation of the substrate cytokines or receptors. Antagonists may be employed for a variety of therapeutic and prophylactic purposes for such conditions as inflammation, neural degeneration, allergic disorders, or other disorders involving a dis-regulation of the substrate cytokines or receptors.

In general, such screening procedures may involve using appropriate cells which express the Human KUZ polypeptide or respond to Human KUZ polypeptide of the present invention. Such cells include cells from mammals, yeast, Drosophila or E. coli. Cells which express the Human KUZ polypeptide (or cell membrane containing the expressed polypeptide) or respond to Human KUZ polypeptide are then contacted with a test compound to observe binding, or stimulation or inhibition of a functional response. The ability of the cells which were contacted with the candidate compounds is compared with the same cells which were not contacted for Human KUZ activity.

Enzymatic activity or inhibition of activity can be measured using any of the standard methods for proteases: for example, fluorescence quenched substrate based on protein sequence; scintillation proximity assays using biotinylated and radioactively labelled peptides, Western blots or ELISAs directed at product proteins.

The assays may simply test binding of a candidate compound wherein adherence to the cells bearing the Human KUZ polypeptide is detected by means of a label directly or indirectly associated with the candidate compound or in an assay involving competition with a labeled competitor. Further, these assays may test whether the candidate compound results in a signal generated by activation of the Human KUZ polypeptide, using detection systems appropriate to the cells bearing the Human KUZ polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a Human KUZ polypeptide to form a mixture, measuring Human KUZ activity in the mixture, and comparing the Human KUZ activity of the mixture to a standard.

The Human KUZ cDNA, protein and antibodies to the protein may also be used to configure assays for detecting the effect of added compounds on the production of Human KUZ mRNA and protein in cells. For example, an ELISA may be constructed for measuring secreted or cell associated levels of Human KUZ protein using monoclonal and polyclonal antibodies by standard methods known in the art, and this can be used to discover agents which may inhibit or enhance the production of Human KUZ (also called antagonist or agonist, respectively) from suitably manipulated cells or tissues.

The Human KUZ protein may be used to identify membrane bound or soluble receptors, if any, through standard receptor binding techniques known in the art. These include, but are not limited to, ligand binding and crosslinking assays in which the Human KUZ is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of Human KUZ which compete with the binding of Human KUZ to its receptors, if any. Standard methods for conducting screening assays are well understood in the art.

Examples of potential Human KUZ polypeptide antagonists include antibodies or, in some cases, oligonucleotides or proteins which are closely related to the ligands, substrates, receptors, enzymes, etc., as the case may be, of the Human KUZ polypeptide, e.g., a fragment of the ligands, substrates, receptors, enzymes, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for Human KUZ polypeptides; or compounds which decrease or enhance the production of Human KUZ polypeptides, which comprises:

(a) a Human KUZ polypeptide, preferably that of SEQ ID NO: 2;

(b) a recombinant cell expressing a Human KUZ polypeptide, preferably that of SEQ ID NO: 2;

(c) a cell membrane expressing a Human KUZ polypeptide; preferably that of SEQ ID NO: 2; or (d) antibody to a Human KUZ polypeptide, preferably that of SEQ ID NO: 2.

It will be appreciated that in any such kit, (a), (b), (c) or (d) may comprise a substantial component.

Prophylactic and Therapeutic Methods

This invention provides methods of treating abnormal conditions such as, inflammation, neural degeneration, allergic disorders, or other disorders involving a dis-regulation of the substrate cytokines or receptors, related to both an excess of and insufficient amounts of Human KUZ polypeptide activity.

If the activity of Human KUZ polypeptide is in excess, several approaches are available. One approach comprises administering to a subject an inhibitor compound (antagonist) as hereinabove described along with a pharmaceutically acceptable carrier in an amount effective to inhibit the function of the Human KUZ polypeptide, such as, for example, by blocking the binding of ligands, substrates, receptors, enzymes, etc., or by inhibiting a second signal, and thereby alleviating the abnormal condition. In another approach, soluble forms of Human KUZ polypeptides still capable of binding the ligand, substrate, enzymes, receptors, etc. in competition with endogenous Human KUZ polypeptide may be administered. Typical embodiments of such competitors comprise fragments of the Human KUZ polypeptide.

In still another approach, expression of the gene encoding endogenous Human KUZ polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of Human KUZ and its activity, several approaches are also available. One approach comprises administering to a subject a therapeutically effective amount of a compound which activates Human KUZ polypeptide, i.e., an agonist as described above, in combination with a pharmaceutically acceptable carrier, to thereby alleviate the abnormal condition. Alternatively, gene therapy may be employed to effect the endogenous production of Human KUZ by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of Human KUZ polypeptides in combination with a suitable pharmaceutical carrier.

Formulation and Administration

Peptides, such as the soluble form of Human KUZ polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

The HGS database was searched using the 5' end of the coding region of the bovine disintegrin-metalloprotease gene. The EST 1759347, with Project ID:HSYAG89, was identified from a human thymus stromal cell cDNA library, and the entire insert of this EST was sequenced and determined that it contains the missing 5' end of the published human KUZ gene (Howard L., et al, Biochem. J. 317 (Pt 1), 45–50, 1996). Also, an internal insertion of 153 nucleotide residues located at nucleotide position 160 in the published, partial human KUZ gene, but not present in the bovine homolog, is not present in HSYAG89. Thus, HSYAG89 is the human counterpart to the bovine disintegrin-metalloprotease related to Drosophila KUZ gene.

Northern blots were then carried out using an Apa I, Not I double digest, yielding a 3.5 kb fragment of the coding sequence, which was isolated by gel electrophoresis and radioactively labeled. This fragment was used to detect the coding sequence on multiple tissue blots (Clonetech). These blots show broad expression of the mRNA encoding human KUZ; highest expression is seen in heart, brain, pancreas and thymus. Potential substrates could be identified by co-expression of the substrate in 293 or comparable cells and detecting product protein fragments in the cell supernatant.

Example 2

While there are several methods to obtain the full length cDNA, two are outlined below.

1) The method of Rapid Amplification of cDNA Ends (RACE) can be utilized to obtain the 5' end. See Frohman et al., Proc. Nat. Acad. Sci USA 85, 8998–9002. (1988). Briefly, specific oliognucleotides are annealed to mRNA and used to prime the synthesis of the cDNA strand. Following destruction of the mRNA with RNaseH, a poly C anchor sequence is added to the 3' end of the cDNA and the resulting fragment is amplified using a nested set of antisense primers and an anchor sequence primer. The amplified fragment is cloned into an appropriate vector and subjected to restriction and sequence analysis.

2) The polymerase chain reaction can be used to amplify the 5' end of the cDNA from human cDNA libraries using sequential rounds of nested PCR with two sets of primers. One set of antisense primers is specific to the 5' end of the partial cDNA and the other set of primers anneals to vector specific sequence. The amplified products are cloned into an appropriate vector and subjected to restriction and sequence analysis.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence that encodes the Human KUZ polypeptide of SEQ ID NO: 2.

2. The isolated polynucleotide of claim 1 wherein said polynucleotide comprises the nucleotide sequence contained in SEQ ID NO: 1 encoding the Human KUZ polypeptide of SEQ ID NO: 2.

3. The isolated polynucleotide of claim 1 wherein said polynucleotide comprises the nucleotide sequence as set forth in SEQ ID NO: 1.

4. The isolated polynucleotide of claim 3 which is polynucleotide of SEQ ID NO: 1.

5. An expression system comprising an isolated DNA or RNA molecule, wherein said expression system produces a Human KUZ polyptide comprising an amino acid sequence as set forth in SEQ ID NO: 2 when said expression system is present in a compatible host cell.

6. An isolated host cell comprising the expression system of claim 5.

7. A process for producing a Human KUZ polypeptide comprising culturing the isolated host of claim 6 under conditions sufficient for the production of said polypeptide and recovering the polypeptide from the culture.

8. A process for producing a host cell which produces the Human KUZ polypeptide thereof comprising transforming or transfecting the host cell with the expression system of claim 5 such that the host cell, under appropriate culture conditions, produces the Human KUZ polypeptide.

9. An isolated Human KUZ polypeptide comprising an amino acid sequence which is the amino acid sequence as set forth in SEQ ID NO: 2.

10. The polypeptide of claim 9 consisting of the amino acid sequence of SEQ ID NO: 2.

11. An antibody immunospecific for a Human KUZ polypeptide comprising the amino acid sequence of SEQ ID NO: 2.

12. The host cell produced by the method of claim 8 expressing the Human KUZ polypeptide, or the membrane thereof.

13. The isolated polynucleotide of claim 1 wherein said nucleotide sequence comprises the entire coding region of SEQ ID NO: 1.

14. The isolated polynucleotide of claim 1 wherein said nucleotide sequence is the entire length of the RNA transcript of SEQ ID NO: 1.

15. The isolated polynucleotide of claim 1 wherein said nucleotide sequence is the coding region of the RNA transcript of SEQ ID NO: 1.

16. A isolated polynucleotide obtained by screening an appropriate library under stringent hybridization conditions with a probe having the sequence of SEQ ID NO: 1, said stringent hybridization conditions comprising overnight incubation of filters at 42° C. in a solution comprising: 50% formamide, 5×SSC, 50 mM sodium phosphate having pH 7.6, 5×Denhardt's solution, 10% dextran sulfate, and 20 micrograms per ml of denatured, sheared salmon sperm DNA, followed by washing the filters in 0.1×SSC at 65° C.

17. A membrane of the recombinant host cell of claim 6 expressing a polypeptide comprising an amino acid sequence as set forth in SEQ ID NO: 2.

18. A polynucleotide sequence which is the complement to any of the isolated polynucleotides in any one of claims 1–4, 5, 13, 14, 15, or 16.

19. A method for detecting mutations comprising:

(a) isolating DNA from a subject; and (b) comparing the sequence of said DNA therefrom to that of SEQ ID NO: 1.

20. The isolated polynucleotide of any one of claims 1–4 or 13 which is DNA or RNA.

\* \* \* \* \*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 3349 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
GTCCCGGCTT CCCGTGGAGG CTCCGGACCA AGCCCCTTCA GCTTCTCCCT CCGGATCGAT    60

GTGCTGCTGT TAACCCGTGA GGAGGCGGCG GCGGCGGCAG CGGCAGCGGA AGATGGTGTT   120

GCTGAGAGTG TTAATTCTGC TCCTCTCCTG GGCGGCGGGG ATGGGAGGTC AGTATGGGAA   180

TCCTTTAAAT AAATATATCA GACATTATGA AGGATTATCT ACAATGTGG ATTCATTACA    240

CCAAAAACAC CAGCGTGCCA AAAGAGCAGT CTCACATGAA GACCAATTTT TACGTCTAGA   300

TTTCCATGCC CATGGAAGAC ATTTCAACCT ACGAATGAAG AGGGACACTT CCCTTTTCAG   360

TGATGAATTT AAAGTAGAAA CATCAAATAA AGTACTTGAT TATGATACCT CTCATATTTA   420

CACTGGACAT ATTTTATGGTG AAGAAGGAAG TTTTAGCCAT GGGTCTGTTA TTGATGGAAG   480

ATTTGAAGGA TTCATCCAGA CTCGTGGTGG CACATTTTAT GTTGAGCCAG CAGAGAGATA   540

TATTAAAGAC CGAACTCTGC CATTTCACTC TGTCATTTAT CATGAAGATG ATATTAACTA   600

TCCCCATAAA TACGGTCCTC AGGGGGGCTG TGCAGATCAT TCAGTATTTG AAAGAATGAG   660

GAAATACCAG ATGACTGGTG TAGAGGAAGT AACACAGATA CCTCAAGAAG AACATGCTGC   720

TAATGGTCCA GAACTTCTGA GGAAAAAACG TACAACTTCA GCTGAAAAAA ATACTTGTCA   780

GCTTTATATT CAGACTGATC ATTTGTTCTT TAAATATTAC GGAACACGAG AAGCTGTGAT   840

TGCCCAGATA TCCAGTCATG TTAAAGCGAT TGATACAATT TACCAGACCA CAGACTTCTC   900

CGGAATCCGT AACATCAGTT TCATGGTGAA ACGCATAAGA ATCAATACAA CTGCTGATGA   960

GAAGGACCCT ACAAATCCTT TCCGTTTCCC AAATATTGGT GTGGAGAAGT TTCTGGAATT  1020

GAATTCTGAG CAGAATCATG ATGACTACTG TTTGGCCTAT GTCTTCACAG ACCGAGATTT  1080

TGATGATGGC GTACTTGGTC TGGCTTGGGT TGGAGCACCT TCAGGAAGCT CTGGAGGAAT  1140

ATGTGAAAAA AGTAAACTCT ATTCAGATGG TAAGAAGAAG TCCTTAAACA CTGGAATTAT  1200

TACTGTTCAG AACTATGGGT CTCATGTACC TCCCAAAGTC TCTCACATTA CTTTTGCTCA  1260

CGAAGTTGGA CATAACTTTG GATCCCCACA TGATTCTGGA ACAGAGTGCA CACCAGGAGA  1320

ATCTAAGAAT TTGGGTCAAA AAGAAAATGG CAATTACATC ATGTATGCAA GAGCAACATC  1380

TGGGGACAAA CTTAACAACA ATAAATTCTC ACTCTGTAGT ATTAGAAATA TAAGCCAAGT  1440

TCTTGAGAAG AAGAGAAACA ACTGTTTTGT TGAATCTGGC CAACCTATTT GTGGAAATGG  1500

AATGGTAGAA CAAGGTGAAG AATGTGATTG TGGCTATAGT GACCAGTGTA AAGATGAATG  1560

CTGCTTCGAT GCAAATCAAC CAGAGGGAAG AAAATGCAAA CTGAAACCTG GAAACAGTG   1620

CAGTCCAAGT CAAGGTCCTT GTTGTACAGC ACAGTGTGCA TTCAAGTCAA AGTCTGAGAA  1680

GTGTCGGGAT GATTCAGACT GTGCAAGGGA AGGAATATGT AATGGCTTCA CAGCTCTCTG  1740

CCCAGCATCT GACCCTAAAC CAAACTTCAC AGACTGTAAT AGGCATACAC AAGTGTGCAT  1800
```

```
TAATGGGCAA TGTGCAGGTT CTATCTGTGA GAAATATGGC TTAGAGGAGT GTACGTGTGC   1860

CAGTTCTGAT GGCAAAGATG ATAAAGAATT ATGCCATGTA TGCTGTATGA AGAAAATGGA   1920

CCCATCAACT TGTGCCAGTA CAGGGTCTGT GCAGTGGAGT AGGCACTTCA GTGGTCGAAC   1980

CATCACCCTG CAACCTGGAT CCCCTTGCAA CGATTTTAGA GGTTACTGTG ATGTTTTCAT   2040

GCGGTGCAGA TTAGTAGATG CTGATGGTCC TCTAGCTAGG CTTAAAAAAG CAATTTTTAG   2100

TCCAGAGCTC TATGAAAACA TTGCTGAATG GATTGTGGCT CATTGGTGGG CAGTATTACT   2160

TATGGGAATT GCTCTGATCA TGCTAATGGC TGGATTTATT AAGATATGCA GTGTTCATAC   2220

TCCAAGTAGT AATCCAAAGT TGCCTCCTCC TAAACCACTT CCAGGCACTT TAAAGAGGAG   2280

GAGACCTCCA CAGCCCATTC AGCAACCCCA GCGTCAGCGG CCCCGAGAGA GTTATCAAAT   2340

GGGACACATG AGACGCTAAC TGCAGCTTTT GCCTTGGTTC TTCCTAGTGC CTACAATGGG   2400

AAAACTTCAC TCCAAAGAGA AACCTATTAA GTCATCATCT CCAAACTAAA CCCTCACAAG   2460

TAACAGTTGA AGAAAAAATG GCAAGAGATC ATATCCTCAG ACCAGGTGGA ATTACTTAAA   2520

TTTTAAAGCC TGAAAATTCC AATTTGGGGG TGGGAGGTGG AAAAGGAACC CAATTTTCTT   2580

ATGAACAGAT ATTTTTAACT TAATGGCACA AAGTCTTAGA ATATTATTAT GTGCCCCGTG   2640

TTCCCTGTTC TTCGTTGCTG CATTTTCTTC ACTTGCAGGC AAACTTGGCT CTCAATAAAC   2700

TTTTACCACA AATTGAAATA AATATATTTT TTTCAACTGC CAATCAAGGG TAGGAGGCTC   2760

GACCACCTCA ACATTGGAGA CATCACTTGC CAATGTACAT ACCTTGTTAT ATGCAGACAT   2820

GTATTTCTTA CGTACACTGT ACTTCTGTGT GCAATTGTAA ACAGAAATTG CAATATGGAT   2880

GTTTCTTTGT ATTATAAAAT TTTTCCGCTC TTAATTAAAA ATTACTGTTT AATTGACATA   2940

CTCAGGATAA CAGAGAATGG TGGTATTCAG TGGTCCAGGA TTCTGTAATG CTTTACACAG   3000

GCAGTTTTGA ATGAAAATC AATTTACCTT TCTGTTACGA TGGAGTTGGT TTTGATACTC   3060

ATTTTTCTT TATCACATGG CTGCTACGGG CACAAGTGAC TATACTGAAG AACACAGTTA   3120

AGTGTTGTGC AAACTGGACA TAGCAGCACA TACTACTTCA GAGTTCATGA TGTAGATGTC   3180

TGGTTTCTGC TTACGTCTTT TAAACTTTCT AATTCAATTC CATTTTTCAA TTAATAGGTG   3240

AAATTTTATT CATGCTTTGA TAGAAATTAT GTCAATGAAA TGAAAAAAAA AAAAAAAGG   3300

GCGGCCGCTC TAGAGGATCC CTCGAGGGGC CCAAGCTTAC GCGTGCATG              3349
```

(2) INFORMATION FOR SEQ ID NO:2:

(i) SEQUENCE CHARACTERISTICS:
        (A) LENGTH: 748 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Val Leu Leu Arg Val Leu Ile Leu Leu Leu Ser Trp Ala Ala Gly
 1               5                  10                  15

Met Gly Gly Gln Tyr Gly Asn Pro Leu Asn Lys Tyr Ile Arg His Tyr
                20                  25                  30

Glu Gly Leu Ser Tyr Asn Val Asp Ser Leu His Gln Lys His Gln Arg
            35                  40                  45

Ala Lys Arg Ala Val Ser His Glu Asp Gln Phe Leu Arg Leu Asp Phe
        50                  55                  60

His Ala His Gly Arg His Phe Asn Leu Arg Met Lys Arg Asp Thr Ser
65                  70                  75                  80
```

-continued

```
Leu Phe Ser Asp Glu Phe Lys Val Glu Thr Ser Asn Lys Val Leu Asp
                 85                  90                  95
Tyr Asp Thr Ser His Ile Tyr Thr Gly His Ile Tyr Gly Glu Glu Gly
            100                 105                 110
Ser Phe Ser His Gly Ser Val Ile Asp Gly Arg Phe Glu Gly Phe Ile
            115                 120                 125
Gln Thr Arg Gly Gly Thr Phe Tyr Val Glu Pro Ala Glu Arg Tyr Ile
        130                 135                 140
Lys Asp Arg Thr Leu Pro Phe His Ser Val Ile Tyr His Glu Asp Asp
145                 150                 155                 160
Ile Asn Tyr Pro His Lys Tyr Gly Pro Gln Gly Gly Cys Ala Asp His
                165                 170                 175
Ser Val Phe Glu Arg Met Arg Lys Tyr Gln Met Thr Gly Val Glu Glu
            180                 185                 190
Val Thr Gln Ile Pro Gln Glu Glu His Ala Ala Asn Gly Pro Glu Leu
            195                 200                 205
Leu Arg Lys Lys Arg Thr Thr Ser Ala Glu Lys Asn Thr Cys Gln Leu
        210                 215                 220
Tyr Ile Gln Thr Asp His Leu Phe Phe Lys Tyr Gly Thr Arg Glu
225                 230                 235                 240
Ala Val Ile Ala Gln Ile Ser Ser His Val Lys Ala Ile Asp Thr Ile
                245                 250                 255
Tyr Gln Thr Thr Asp Phe Ser Gly Ile Arg Asn Ile Ser Phe Met Val
            260                 265                 270
Lys Arg Ile Arg Ile Asn Thr Thr Ala Asp Glu Lys Asp Pro Thr Asn
        275                 280                 285
Pro Phe Arg Phe Pro Asn Ile Gly Val Glu Lys Phe Leu Glu Leu Asn
        290                 295                 300
Ser Glu Gln Asn His Asp Asp Tyr Cys Leu Ala Tyr Val Phe Thr Asp
305                 310                 315                 320
Arg Asp Phe Asp Asp Gly Val Leu Gly Leu Ala Trp Val Gly Ala Pro
                325                 330                 335
Ser Gly Ser Ser Gly Gly Ile Cys Glu Lys Ser Lys Leu Tyr Ser Asp
            340                 345                 350
Gly Lys Lys Lys Ser Leu Asn Thr Gly Ile Ile Thr Val Gln Asn Tyr
        355                 360                 365
Gly Ser His Val Pro Pro Lys Val Ser His Ile Thr Phe Ala His Glu
    370                 375                 380
Val Gly His Asn Phe Gly Ser Pro His Asp Ser Gly Thr Glu Cys Thr
385                 390                 395                 400
Pro Gly Glu Ser Lys Asn Leu Gly Gln Lys Glu Asn Gly Asn Tyr Ile
                405                 410                 415
Met Tyr Ala Arg Ala Thr Ser Gly Asp Lys Leu Asn Asn Asn Lys Phe
            420                 425                 430
Ser Leu Cys Ser Ile Arg Asn Ile Ser Gln Val Leu Glu Lys Lys Arg
        435                 440                 445
Asn Asn Cys Phe Val Glu Ser Gly Gln Pro Ile Cys Gly Asn Gly Met
    450                 455                 460
Val Glu Gln Gly Glu Glu Cys Asp Cys Gly Tyr Ser Asp Gln Cys Lys
465                 470                 475                 480
Asp Glu Cys Cys Phe Asp Ala Asn Gln Pro Glu Gly Arg Lys Cys Lys
                485                 490                 495
Leu Lys Pro Gly Lys Gln Cys Ser Pro Ser Gln Gly Pro Cys Cys Thr
            500                 505                 510
```

```
Ala Gln Cys Ala Phe Lys Ser Lys Ser Glu Lys Cys Arg Asp Asp Ser
        515                 520                 525

Asp Cys Ala Arg Glu Gly Ile Cys Asn Gly Phe Thr Ala Leu Cys Pro
    530                 535                 540

Ala Ser Asp Pro Lys Pro Asn Phe Thr Asp Cys Asn Arg His Thr Gln
545                 550                 555                 560

Val Cys Ile Asn Gly Gln Cys Ala Gly Ser Ile Cys Glu Lys Tyr Gly
            565                 570                 575

Leu Glu Glu Cys Thr Cys Ala Ser Ser Asp Gly Lys Asp Asp Lys Glu
            580                 585                 590

Leu Cys His Val Cys Cys Met Lys Lys Met Asp Pro Ser Thr Cys Ala
        595                 600                 605

Ser Thr Gly Ser Val Gln Trp Ser Arg His Phe Ser Gly Arg Thr Ile
    610                 615                 620

Thr Leu Gln Pro Gly Ser Pro Cys Asn Asp Phe Arg Gly Tyr Cys Asp
625                 630                 635                 640

Val Phe Met Arg Cys Arg Leu Val Asp Ala Asp Gly Pro Leu Ala Arg
            645                 650                 655

Leu Lys Lys Ala Ile Phe Ser Pro Glu Leu Tyr Glu Asn Ile Ala Glu
            660                 665                 670

Trp Ile Val Ala His Trp Trp Ala Val Leu Leu Met Gly Ile Ala Leu
        675                 680                 685

Ile Met Leu Met Ala Gly Phe Ile Lys Ile Cys Ser Val His Thr Pro
    690                 695                 700

Ser Ser Asn Pro Lys Leu Pro Pro Pro Lys Pro Leu Pro Gly Thr Leu
705                 710                 715                 720

Lys Arg Arg Arg Pro Pro Gln Pro Ile Gln Gln Pro Gln Arg Gln Arg
            725                 730                 735

Pro Arg Glu Ser Tyr Gln Met Gly His Met Arg Arg
            740                 745
```